(12) United States Patent
Ono (10) Patent No.: US 8,967,804 B2
(45) Date of Patent: Mar. 3, 2015

(54) OPHTHALMIC APPARATUS, OPHTHALMIC APPARATUS CONTROL METHOD AND STORAGE MEDIUM

(71) Applicant: Canon Kabushiki Kaisha, Tokyo (JP)

(72) Inventor: Shigeaki Ono, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 13/744,529

(22) Filed: Jan. 18, 2013

(65) Prior Publication Data

US 2013/0194545 A1    Aug. 1, 2013

(30) Foreign Application Priority Data

Jan. 26, 2012    (JP) .................................. 2012-014581

(51) Int. Cl.
*A61B 3/14*        (2006.01)
*A61B 3/00*        (2006.01)

(52) U.S. Cl.
CPC .................................... *A61B 3/0091* (2013.01)
USPC ....................................................... 351/206

(58) Field of Classification Search
USPC ........................... 351/205, 206, 211–216, 221
See application file for complete search history.

(56) References Cited

U.S. PATENT DOCUMENTS

| 6,273,565 | B1 * | 8/2001 | Matsumoto ................... 351/210 |
| 2003/0138776 | A1 * | 7/2003 | Goldman et al. ................. 435/6 |
| 2003/0234908 | A1 | 12/2003 | Kushida |
| 2004/0075814 | A1 * | 4/2004 | Alster et al. ................... 351/246 |
| 2006/0082728 | A1 * | 4/2006 | Kushida ......................... 351/211 |
| 2011/0304821 | A1 | 12/2011 | Tanassi et al. |

FOREIGN PATENT DOCUMENTS

| CN | 101677761 A | 3/2010 |
| JP | 2003-000546 A | 1/2003 |
| JP | 2011-050430 A | 3/2011 |
| JP | 2011-206519 A | 10/2011 |
| JP | 2011-255045 A | 12/2011 |
| WO | 2011111851 A1 | 9/2011 |

OTHER PUBLICATIONS

Chinese Office Action issued in corresponding application No. 201310033047.3 on Aug. 4, 2014.

* cited by examiner

*Primary Examiner* — Mahidere Sahle
(74) *Attorney, Agent, or Firm* — Carter, DeLuca, Farrell & Schmidt, LLP

(57) ABSTRACT

An ophthalmic apparatus comprises: an image obtaining unit configured to obtain a fundus image of an eye to be examined; an information obtaining unit configured to obtain, from the fundus image, information about the eye to be examined; a fixation target display unit configured to display a fixation target pattern; and a change unit configured to change, in accordance with the information about the eye to be examined, the fixation target pattern displayed by the fixation target display unit.

12 Claims, 8 Drawing Sheets

OPHTHALMIC APPARATUS, OPHTHALMIC APPARATUS CONTROL METHOD AND STORAGE MEDIUM

BACKGROUND OF THE INVENTION

1. Field of the Invention

The present invention relates to an ophthalmic apparatus, ophthalmic apparatus control method, and storage medium.

2. Description of the Related Art

Nowadays, various kinds of ophthalmic apparatuses using optical apparatuses have been used. For example, as an optical apparatus for observing an eye, a variety of apparatuses are used, including an anterior ocular segment imaging apparatus, fundus camera, and SLO (Scanning Laser Ophthalmoscope). Of these apparatuses, an optical tomographic imaging apparatus based on OCT (Optical Coherence Tomography) using multi-wavelength light wave interference is an apparatus (to be referred to as an OCT apparatus hereinafter) capable of obtaining a tomogram of a sample at high resolution. The OCT apparatus is becoming indispensable in outpatient clinics specialized in retinas as an ophthalmic apparatus. The OCT apparatus divides measurement light serving as low-coherent light into reference light and measurement light. The OCT apparatus irradiates an object to be examined with the measurement light, and makes return light from the object interfere with the reference light, thereby obtaining a tomogram of the object. In addition, the OCT apparatus can obtain a high-resolution tomogram by scanning a sample with measurement light. The OCT apparatus can therefore obtain a tomogram of a retina on the fundus of an eye to be examined, and has been widely used for ophthalmic diagnosis and the like for the retina. However, when the object to be examined is a living body such as an eye, distortion of an image caused by the movement of the eye becomes problematic. It is needed to measure the eye quickly at high sensitivity without the influence of movement of the eye.

Japanese Patent Laid-Open No. 2011-206519 or No. 2011-50430 discloses the following ophthalmic apparatus. The ophthalmic apparatus extracts the feature point of a fundus image from the first fundus image captured by fundus imaging for obtaining a fundus image. The ophthalmic apparatus further detects a feature point from the second fundus image different from the first fundus image. Based on the coordinates of the respective feature points on the fundus images, the ophthalmic apparatus measures a positional change of the fundus of the eye to be examined.

Japanese Patent Laid-Open No. 2003-546 discloses an ophthalmic apparatus which can display fixation target patterns different in size with a plurality of types of shapes, and stores a fixation target pattern for each eye to be examined.

However, the ophthalmic apparatus disclosed in Japanese Patent Laid-Open No. 2011-206519 or No. 2011-50430 uses a single fixation target. Since the vision is different for each object, the vision fixation of an eye to be examined becomes unstable, and no appropriate fundus image can be obtained.

The ophthalmic apparatus disclosed in Japanese Patent Laid-Open No. 2003-546 can switch and display fixation target patterns different in size with a plurality of types of shapes. However, the user manually switches the fixation target patterns. Changing the fixation target is cumbersome and does not consider the vision fixation state of an eye to be examined. Therefore, time is taken to select a fixation lamp suited to an object, placing a burden on the object.

SUMMARY OF THE INVENTION

To solve the above problems, the present invention provides a technique of stabilizing the vision fixation of an eye to be examined in ophthalmic imaging, and reducing the burden on the user.

According to one aspect of the present invention, there is provided an ophthalmic apparatus comprising: an image obtaining unit configured to obtain a fundus image of an eye to be examined; an information obtaining unit configured to obtain, from the fundus image, information about the eye to be examined; a fixation target display unit configured to display a fixation target pattern; and a change unit configured to change, in accordance with the information about the eye to be examined, the fixation target pattern displayed by the fixation target display unit.

According to one aspect of the present invention, there is provided an ophthalmic apparatus control method comprising the steps of: obtaining a fundus image of an eye to be examined; obtaining, from the fundus image, information about the eye to be examined; and changing, in accordance with the information about the eye to be examined, a fixation target pattern displayed by a fixation target display unit.

Further features of the present invention will be apparent from the following description of exemplary embodiments with reference to the attached drawings.

DESCRIPTION OF THE EMBODIMENTS

An exemplary embodiment(s) of the present invention will now be described in detail with reference to the drawings. It should be noted that the relative arrangement of the components, the numerical expressions and numerical values set forth in these embodiments do not limit the scope of the present invention unless it is specifically stated otherwise.

(First Embodiment)

The first embodiment will describe an arrangement in which whether the vision fixation state of an eye to be examined is good or bad is determined based on the moving amount of a feature point obtained as information about the eye to be examined from a plurality of images of the eye to be examined, and the display form of a fixation target is changed in accordance with the vision fixation state.

<Arrangement of Ophthalmic Apparatus>

Figure 1A:
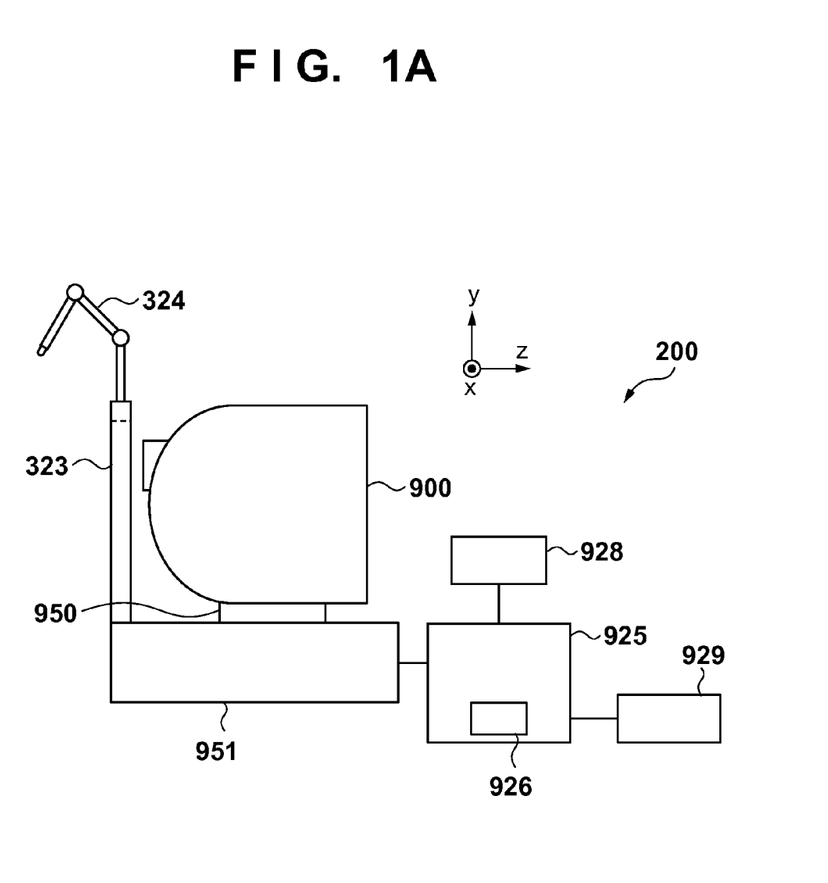
FIGS. 1A and 1B are views exemplifying the arrangement of an ophthalmic apparatus according to the first embodiment.

The schematic arrangement of an ophthalmic apparatus according to the first embodiment will be described with reference to FIG. 1A. An ophthalmic apparatus 200 includes a chin support 323, external fixation target 324, optical head 900, control unit 925, storage unit 926, display unit 928, input acceptance unit 929, stage 950, and base 951.

The chin support 323 fixes the chin and forehead of an object to prompt him to fix his eye (eye to be examined). The external fixation target 324 is used to fix the eye of the object, and can be switched from an internal fixation target (to be described later) and used.

The optical head 900 is a measurement optical system for capturing anterior eye images, two-dimensional images of a fundus, and tomograms. The control unit 925 controls the stage 950, and performs tomogram formation and the like. The storage unit 926 is a hard disk which stores object information, tomography programs, and the like. The display unit 928 displays captured anterior eye images, two-dimensional images of a fundus, tomograms, and the like. The input acceptance unit 929 accepts an instruction from the user to the control unit 925, and is a keyboard, mouse, or the like.

The stage 950 can move the optical head 900 in the X, Y, and Z directions using a motor (not shown). The base 951 supports the stage 950, and incorporates a spectrometer (to be described later).

<Arrangements of Measurement Optical System and Spectrometer>

Next, the arrangement of the measurement optical system of the optical head 900 and that of the spectrometer of the base 951 will be described with reference to FIG. 1B. First, the arrangement of the optical head 900 will be explained. An objective lens 135-1 is arranged to face an eye 107 to be examined. A first dichroic mirror 132-1 and second dichroic mirror 132-2 branch the optical path for respective wavelength bands into an optical path 351 of the OCT optical system, an optical path 352 for fundus observation and a fixation lamp, and an optical path 353 for anterior eye observation. Of lenses 135-3 and 135-4, the lens 135-3 is driven by a motor (not shown) to adjust the focuses of an internal fixation target 191 and fundus observation CCD 172.

A perforated mirror 303 is interposed between the lens 135-4 and a third dichroic mirror 132-3. The perforated mirror 303 branches the optical path 352 into optical paths 352-2 and 354.

The optical path 354 forms an illumination optical system which illuminates the fundus of the eye 107 to be examined. An LED light source 316 is a fundus observation illumination light source used to align the eye 107 to be examined. A stroboscopic tube 314 interposed between condenser lenses 313 and 315 is used to image the fundus of the eye 107 to be examined. A mirror 317 is used to change the direction of the optical path.

Illumination light emitted by the LED light source 316 via the stroboscopic tube 314 is changed into a ring-shaped beam via a ring slit 312. The ring-shaped beam is reflected by the perforated mirror 303 via lenses 311 and 309, and illuminates a retina 127 of the eye 107 to be examined. Note that the LED light source 316 has a central wavelength of about 780 nm.

The optical path 352-2 extending toward the third dichroic mirror 132-3 via the perforated mirror 303 is branched by the third dichroic mirror 132-3 for respective wavelength bands into an optical path extending toward the fundus observation CCD 172 and an optical path extending toward the internal fixation target 191.

The CCD 172 has sensitivity near the central wavelength of the LED light source 316 for fundus observation illumination light, more specifically, 780 nm. A CCD control unit 102 controls the CCD 172. The internal fixation target 191 generates visible light to prompt the vision fixation of an object. A fixation target control unit 103 controls the internal fixation target 191.

The CCD control unit 102 and fixation target control unit 103 are connected to an arithmetic unit 104 of the base 951, and receive and output data from and to the control unit 925 via the arithmetic unit 104.

A lens 135-2 and an infrared CCD 171 for anterior eye observation are arranged on the optical path 353. The infrared CCD 171 has sensitivity near the wavelength of anterior eye observation illumination light (not shown), more specifically, 970 nm. An image splitting prism (not shown) is inserted in the optical path 353 and allows detecting, as a split image in an anterior eye observation image, the distance of the optical head 900 in the Z direction to the eye 107 to be examined.

The optical path 351 forms an OCT optical system, as described above. The optical path 351 is used to capture a tomogram of the fundus of the eye 107 to be examined, more specifically, is used to obtain an interference signal for forming a tomogram.

An X-Y scanner 134 is used to scan the fundus with light along the two, X- and Y-axes. Of lenses 135-5 and 135-6, the lens 135-5 is driven by a motor (not shown) to focus, on the fundus, light which is emitted by a light source 101 and emerges from an optical fiber 131-2 connected to an optical coupler 131. By the focus adjustment, the light reflected by the fundus of the eye 107 to be examined is simultaneously formed into a spot image at the distal end of the optical fiber 131-2, and enters the optical fiber 131-2. Note that an optical fiber 131-1, the optical fiber 131-2, an optical fiber 131-3, and an optical fiber 131-4 are optical fibers of a single mode that are connected to the optical coupler 131 and integrated.

Next, an optical path extending from the light source 101, and the arrangements of a reference optical system and spectrometer 180 will be described. Light emitted by the light source 101 is divided into measurement light toward the optical fiber 131-2 and reference light toward the optical fiber 131-3 via the optical fiber 131-1 and optical coupler 131.

The measurement light irradiates the fundus of the eye 107 to be examined serving as an observation target via the optical path of the above-mentioned OCT optical system. The measurement light is reflected and scattered by the retina, and reaches the optical coupler 131 via the same optical path.

The reference light reaches and is reflected by a fourth dichroic mirror 132-4 via the optical fiber 131-3, a lens 135-7, and a dispersion-compensating glass 115 inserted to make dispersion of the measurement light match that of the reference light. The reference light returns through the same optical path and reaches the optical coupler 131.

The optical coupler 131 combines the measurement light and the reference light, forming interference light. Interference occurs when the optical path lengths of the measurement light and reference light almost coincide with each other. A motor and driving mechanism (neither is shown) hold the fourth dichroic mirror 132-4 so that its position can be adjusted along the optical axis. This allows making the optical path length of reference light match that of measurement light that changes depending on the eye 107 to be examined. The interference light is guided to the spectrometer 180 via the optical fiber 131-4.

A polarization adjusting unit 139-1 is inserted in the optical fiber 131-2 to adjust polarization on the measurement light side. A polarization adjusting unit 139-2 is inserted in the optical fiber 131-3 to adjust polarization on the reference light side. These polarization adjusting units include several looped portions of the optical fibers. The looped portion is pivoted in the longitudinal direction of the fiber to apply torsion to the fiber so that the polarization states of measurement light and reference light can be adjusted to match each other. In the embodiment, the polarization states of measurement light and reference light are adjusted and fixed in advance.

The spectrometer 180 includes a lens 135-8, lens 135-9, diffraction grating 181, and line sensor 182. The interference light emerging from the optical fiber 131-4 is made almost parallel through the lens 135-8, and then spectroscoped by the diffraction grating 181. The lens 135-9 forms the light into an image on the line sensor 182.

The above-described arrangement forms a Michelson interferometer.

Next, the light source 101 will be described. The light source 101 is an SLD (Super Luminescent Diode) which is a typical low-coherent light source. The light source 101 has a central wavelength of 855 nm and a wavelength band width of about 100 nm. The wavelength band width is an important parameter because it affects the resolution of an obtained tomogram along the optical axis. Although the type of light source is the SLD here, ASE (Amplified Spontaneous Emission) or the like is also usable as long as low-coherent light can be emitted. Considering measurement of an eye, the central wavelength is preferably the wavelength of infrared light. In addition, the central wavelength affects the resolution of an obtained tomogram in the lateral direction and thus is preferably short. For the two reasons, the central wavelength is set to 855 nm.

Although the embodiment uses a Michelson interferometer as the interferometer, a Mach-Zehnder interferometer may be used. It is also possible to use a Mach-Zehnder interferometer when the light quantity difference between measurement light and reference light is large, and a Michelson interferometer when it is relatively small.

<Tomogram Capturing Method>

Next, a tomogram capturing method using the ophthalmic apparatus 200 will be explained. The ophthalmic apparatus 200 can capture a tomogram of a desired portion on the fundus of the eye 107 to be examined by controlling the X-Y scanner 134.

Figure 1B:
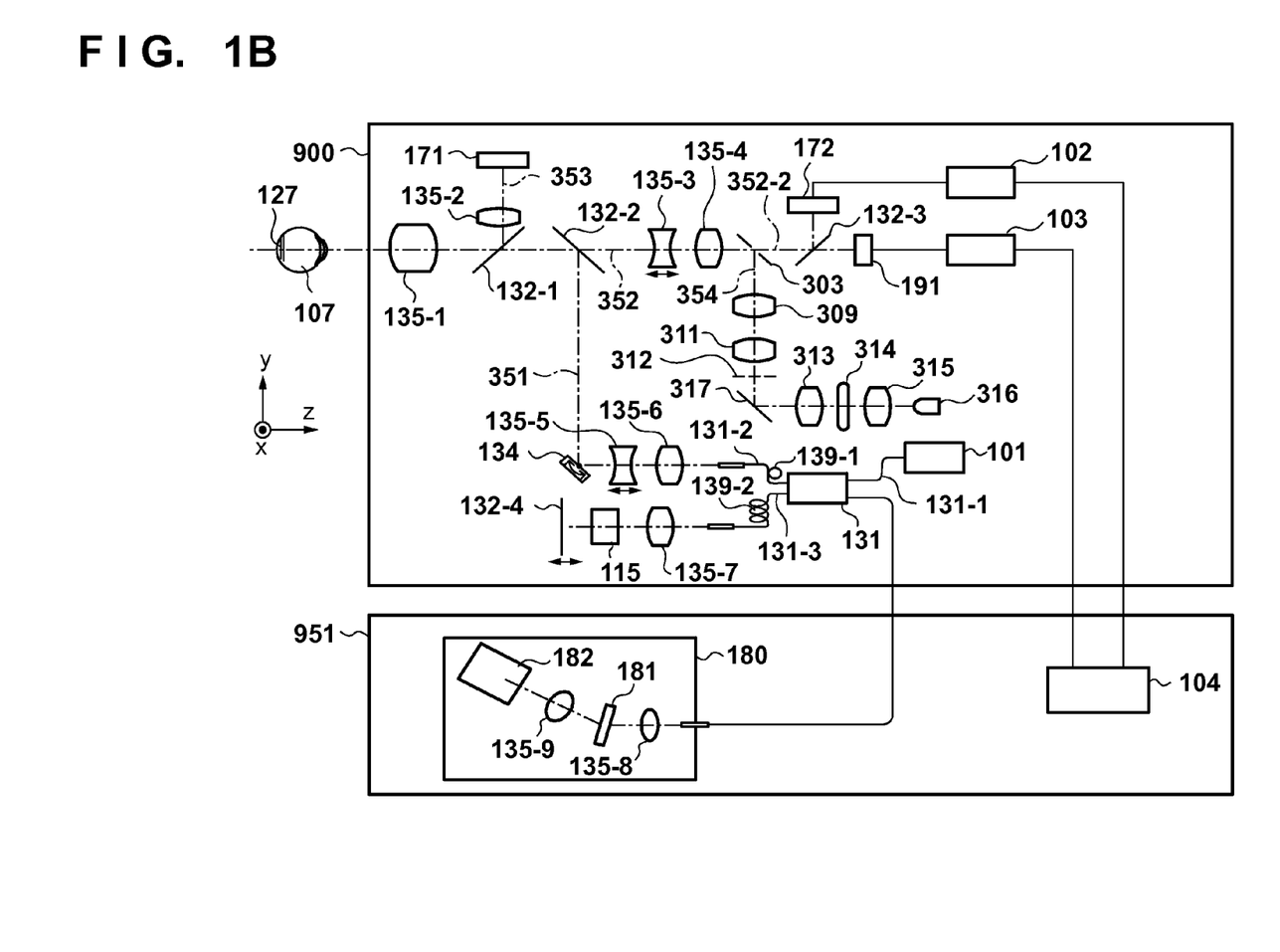

In FIG. 1B, measurement light is scanned in the X direction, and the line sensor 182 obtains information about a predetermined number of captured images in an imaging range in the X direction on the fundus. A luminance distribution on the line sensor 182 that is obtained at a given position in the X direction undergoes FFT (Fast Fourier Transform). A linear luminance distribution obtained by FFT is converted into density or color information to be displayed on the display unit 928. The converted information will be called an A-scan image. A two-dimensional image obtained by aligning a plurality of A-scan images will be called a B-scan image. After capturing a plurality of A-scan images to form one B-scan image, the Y scan position is moved to scan measurement light again in the X direction, and a plurality of B-scan images can be obtained. A plurality of B-scan images or a three-dimensional tomogram formed from a plurality of B-scan images is displayed on the display unit 928. The examiner can use the displayed image for diagnosis of an eye to be examined.

<Measurement Screen>

Figure 2:
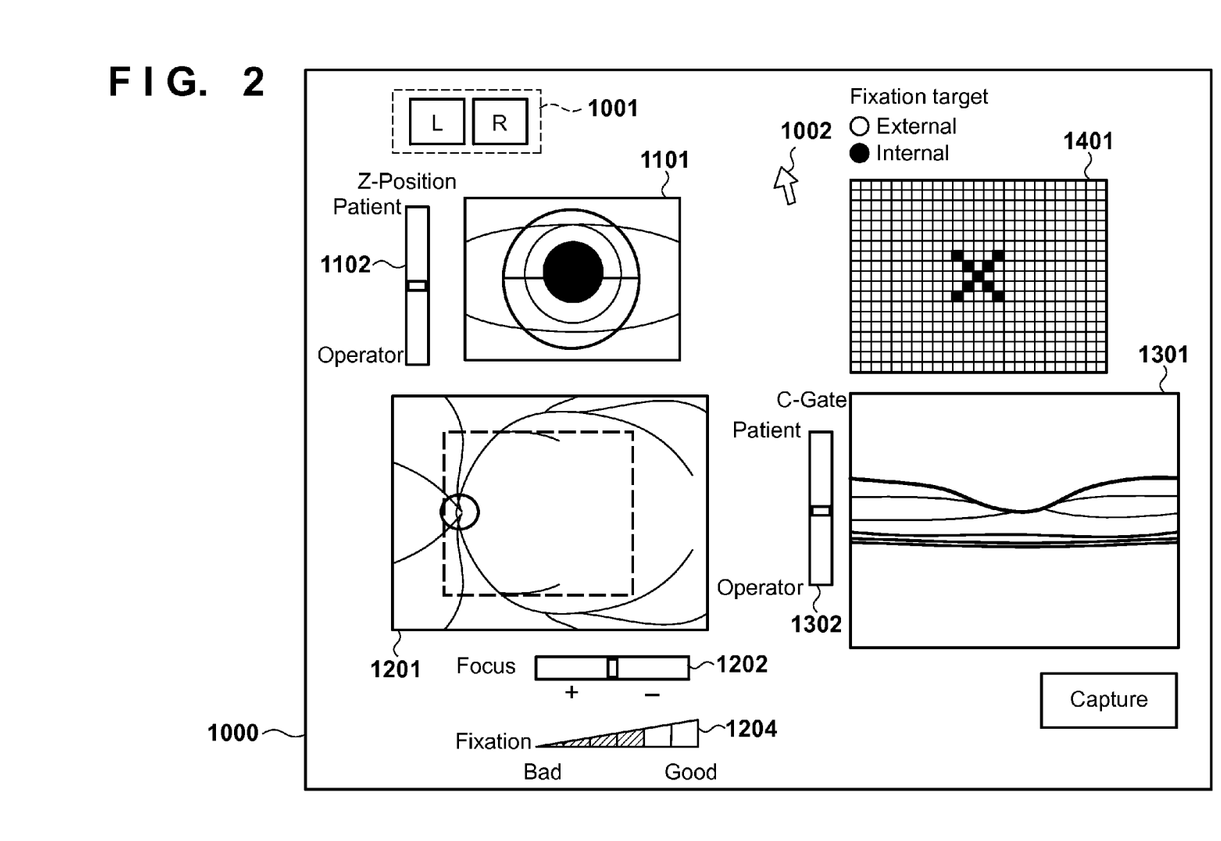
FIG. 2 is a view exemplifying a monitor display screen according to the first embodiment.

FIG. 2 exemplifies a measurement screen 1000 displayed on the display unit 928. The measurement screen 1000 includes an anterior eye observation screen 1101, two-dimensional fundus image display screen 1201, tomogram display screen 1301, and pattern display screen 1401.

The anterior eye observation screen 1101 displays an anterior eye observation image obtained by the anterior eye observation CCD. The two-dimensional fundus image display screen 1201 displays a two-dimensional fundus image obtained by the fundus observation CCD. The tomogram display screen 1301 displays an obtained tomogram. The pattern display screen 1401 displays a pattern formed by the internal fixation target 191.

A switching button 1001 is a button for switching the eye to be examined between the left and right eyes. By pressing L and R buttons, the optical head 900 is moved to the initial positions of the left and right eyes. By operating a mouse included in the input acceptance unit 929, the examiner can move the cursor position of a mouse cursor 1002 on the measurement screen 1000.

A mouse cursor position detector (not shown) calculates the position of the mouse cursor from a pixel position on the display screen. The alignment is configured to be changeable in accordance with the mouse cursor position. More specifically, one or a plurality of predetermined regions in a predetermined range are set in the measurement screen 1000, and the correspondence between the set range and alignment driving is set in advance. When the mouse cursor resides at a pixel in the set range, alignment defined in the set range can be performed. The alignment operation using the mouse can be performed by rotating the mouse wheel.

Sliders arranged near the anterior eye observation screen 1101, two-dimensional fundus image display screen 1201, and tomogram display screen 1301 are used to make various adjustments. A slider 1102 is used to adjust the Z-position of the optical head 900 with respect to the eye 107 to be examined. A slider 1202 is used to adjust the focus. A slider 1302 is used to adjust the position of the coherence gate. The focus adjustment is performed by moving the lenses 135-3 and 135-5 in directions indicated by double-headed arrows in FIG. 1B in order to focus on the fundus. The coherence gate adjustment is performed by moving the fourth dichroic mirror 132-4 in directions indicated by a double-headed arrow in FIG. 1B in order to observe a tomogram at a desired position on the tomogram display screen. These sliders move in synchronism with each other in the alignment operation using the mouse in the respective images.

<Processing by Ophthalmic Apparatus 200>

Illumination light emitted by the LED light source 316 passes through the condenser lenses 315 and 313, is reflected by the mirror 317, and formed into a ring-shaped beam by the ring slit 312. The beam passes through the lenses 311 and 309 and is reflected by the perforated mirror 303. The beam then passes through the lens 135-4, lens 135-3, second dichroic mirror 132-2, first dichroic mirror 132-1, and objective lens 135-1, and illuminates the retina 127 of the eye 107 to be examined.

The light reflected by the retina 127 of the eye 107 to be examined passes through the objective lens 135-1, and passes through the first dichroic mirror 132-1, the second dichroic mirror 132-2, the lens 135-3, the lens 135-4, and the perforated portion of the perforated mirror 303. The light is reflected by the third dichroic mirror 132-3 and forms an image on the CCD 172. The CCD control unit 102 reads out the fundus image formed on the CCD 172, amplifies and A/D-converts it, and outputs the processed fundus image to the arithmetic unit 104. The fundus image input to the arithmetic unit 104 is output to the control unit 925.

Figure 3:
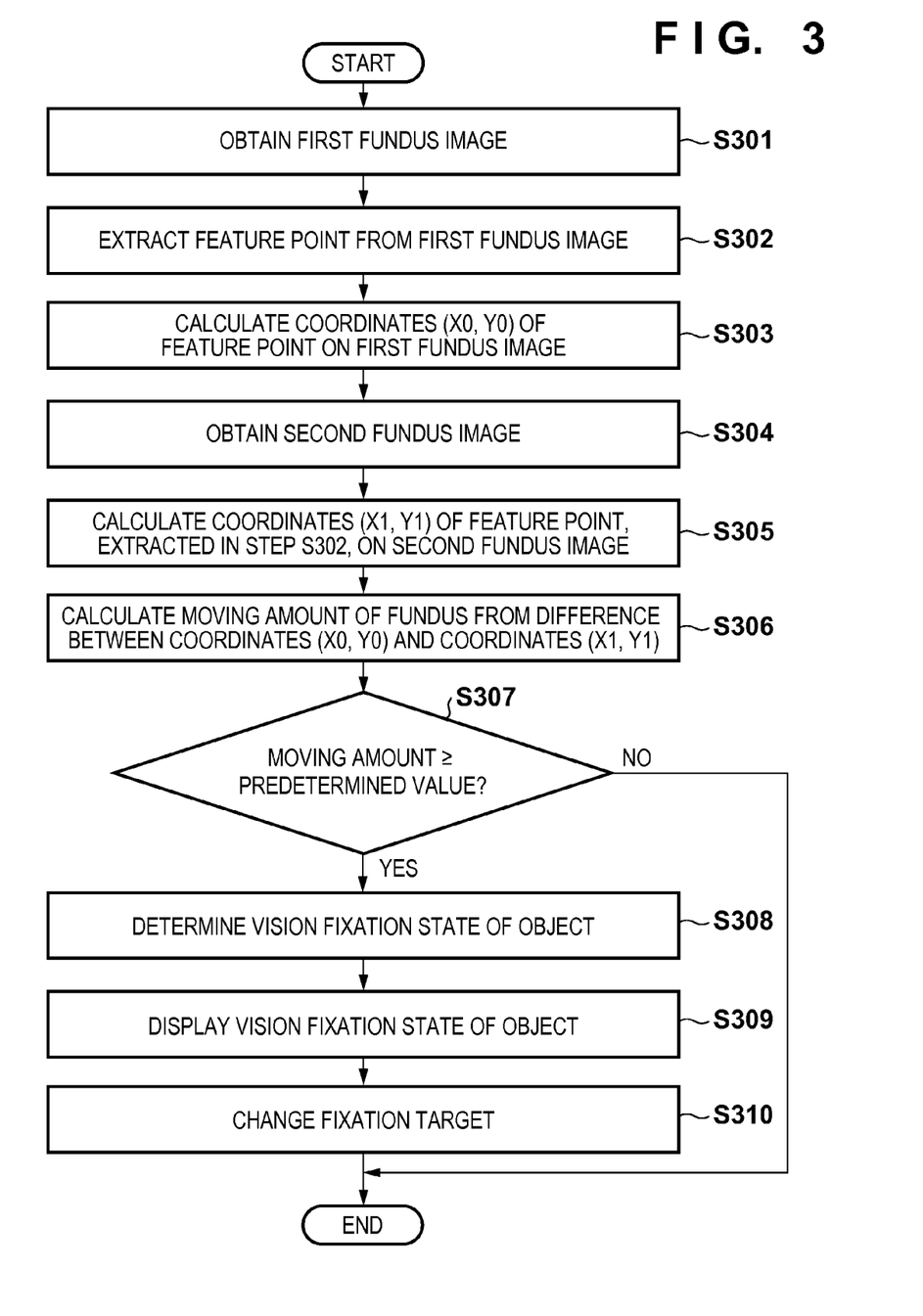
FIG. 3 is a flowchart exemplifying processing procedures by the ophthalmic apparatus according to the first embodiment.

The control unit 925 detects the contrast of the received fundus image, drives the lens 135-3 to a position where the contrast of the fundus becomes highest, and automatically focuses on the fundus of the eye to be examined. Upon completion of focusing on the fundus of the eye to be examined, processing shown in the flowchart of FIG. 3 is executed.

Figure 5:
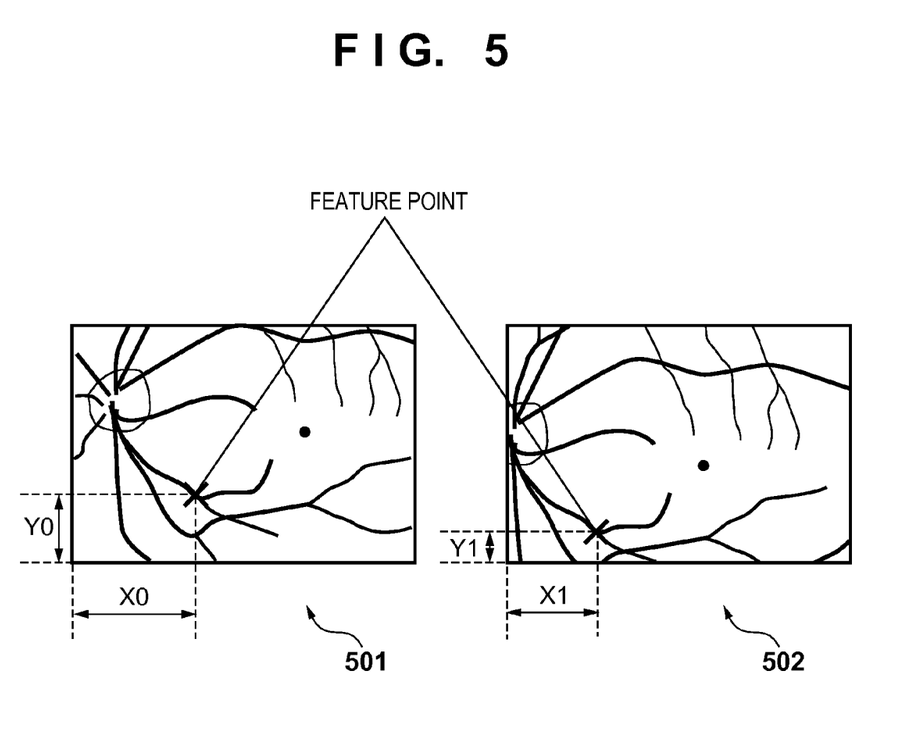
FIG. 5 is a view exemplifying detection of the feature point and moving amount of a fundus image according to the first embodiment.

In step S301, the control unit 925 functioning as an image obtaining unit obtains, as information about an eye to be examined, the first fundus image serving as a reference image for calculating the moving amount of the fundus. In step S302, the control unit 925 extracts a feature point from the first fundus image. The embodiment pays attention to the branch of a fundus blood vessel, and a position as indicated by 501 in FIG. 5 is extracted as a feature point. Note that the feature point is not limited to the branch of a fundus blood vessel. The moving amount may be obtained based on another feature point other than the branch of a fundus blood vessel.

In step S303, the control unit 925 functioning as an information obtaining unit calculates the coordinates (X0, Y0) of the feature point on the first fundus image. In step S304, the control unit 925 functioning as the image obtaining unit obtains the second fundus image. In the embodiment, the fundus image obtaining frame rate is 30 frames/sec, and the second fundus image is obtained after about 33 ms. Note that the frame rate is not limited to this value.

In step S305, the control unit 925 functioning as the information obtaining unit calculates the coordinates (X1, Y1) of a feature point, as indicated by 502 in FIG. 5, on the second fundus image that corresponds to the feature point extracted in step S302.

In step S306, the control unit 925 functioning as the information obtaining unit calculates the difference between the coordinates (X0, Y0) and the coordinates (X1, Y1) (for example, distance value between two coordinate positions or the component value of a difference vector), and sets the difference value as the moving amount of the fundus of the eye to be examined.

In step S307, the control unit 925 determines whether the moving amount of the fundus of the eye to be examined is equal to or larger than a predetermined value. If the control unit 925 determines that the moving amount is equal to or larger than the predetermined value (YES in step S307), the process advances to step S308. If the control unit 925 determines that the moving amount is smaller than the predetermined value (NO in step S307), the process ends. In step S308, the control unit 925 determines the vision fixation state of the eye to be examined.

Figure 6:
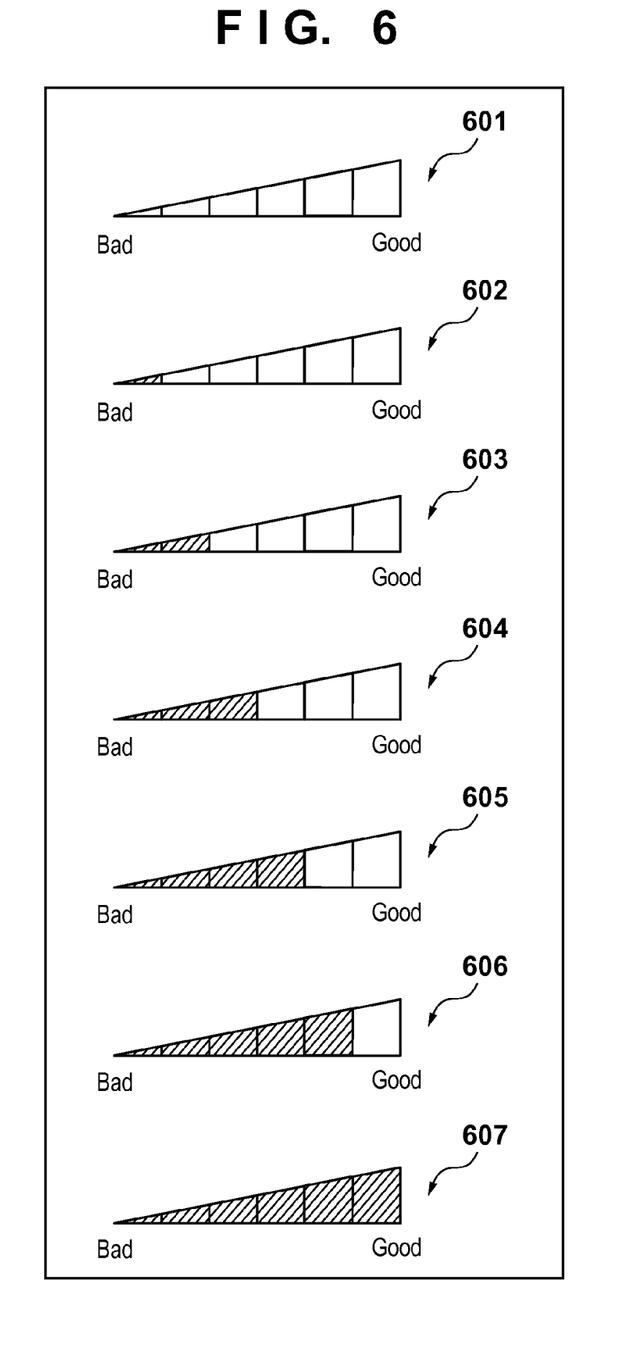
FIG. 6 is a view for explaining an example of an indicator which displays whether the vision fixation state is good or bad according to the first embodiment.

In step S309, the control unit 925 functioning as a change unit and display control unit controls the display unit 928 to change, in accordance with the moving amount, a display form representing the vision fixation state of the eye to be examined, as indicated by an indicator 1204 in FIG. 2. In the embodiment, the indicator 1204 displays, at seven stages indicated by 601 to 607 in FIG. 6, the display form representing the vision fixation state of the eye to be examined. Reference numeral 601 denotes the worst vision fixation state. The vision fixation of the eye to be examined is improved in the order of 602, 603, 604, 605, and 606. Reference numeral 607 denotes the best vision fixation state. Values of the moving amount are classified into, for example, seven ranges. Then, the current vision fixation state is determined by determining a range within which the current value of the moving amount falls. Based on the determination, the vision fixation state of the eye to be examined is displayed. By referring to the indicator 1204, the examiner can easily grasp the vision fixation state of the object, and appropriately switch the fixation target. Hence, the vision fixation of the eye to be examined can be stabilized to shorten the measurement time, reducing the burden on the object.

Figure 4:
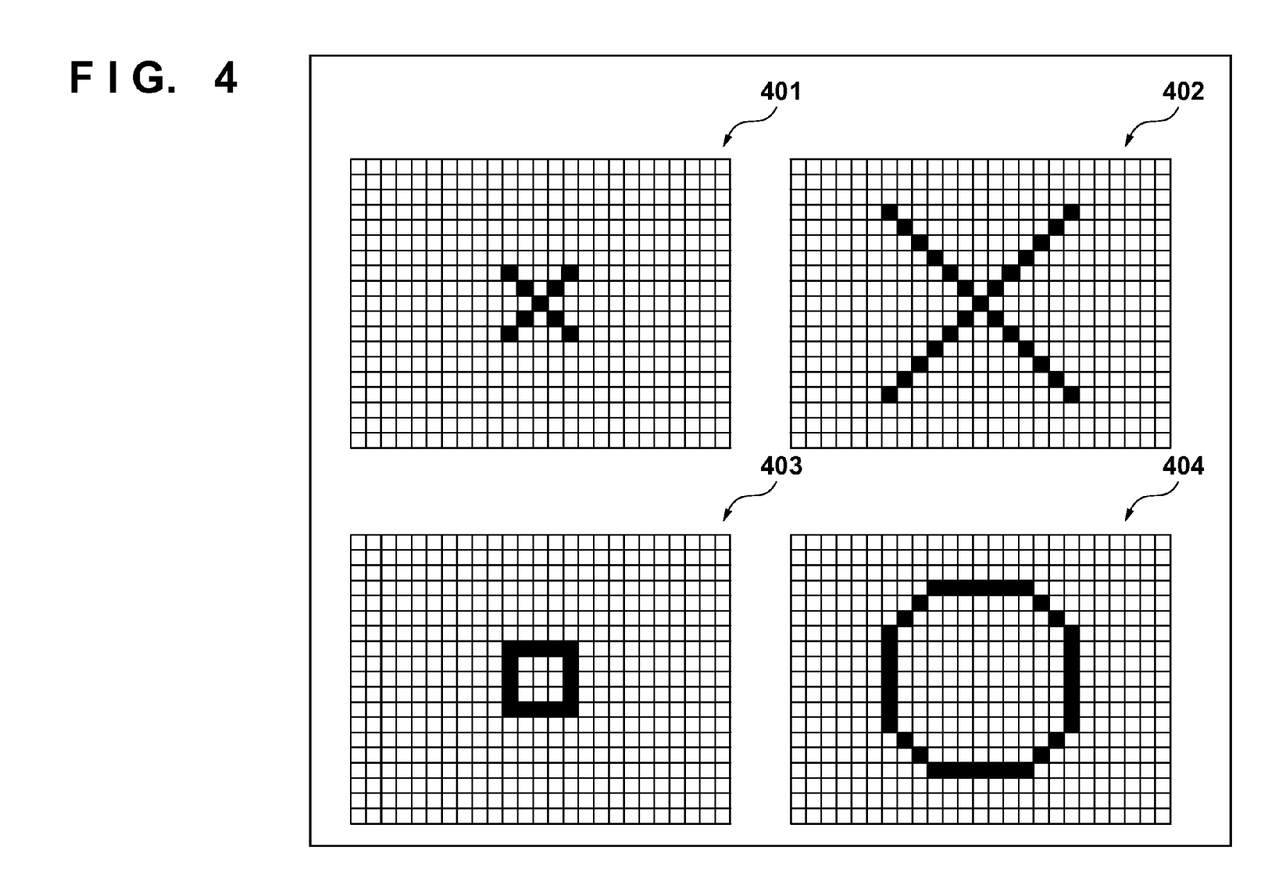
FIG. 4 is a view exemplifying the display pattern of an internal fixation target according to the first embodiment.

In step S310, the control unit 925 functioning as the change unit changes the size, shape, or the like of the fixation target pattern in accordance with the moving amount, and displays the fixation target pattern on the display unit 928 functioning as a fixation target display unit. Patterns 401 to 404 in FIG. 4 are examples of fixation target display patterns of the internal fixation target 191. In the embodiment, the initial value of the fixation target display pattern of the internal fixation target 191 is a display represented by the pattern 401. Note that the initial value is not limited to the fixation target represented by the pattern 401. For example, the initial value may have a size or shape different from the fixation target represented by the pattern 401.

In step S310, for example, the control unit 925 changes the size to be large without changing the shape, as represented by the pattern 402. When changing the size or shape of the fixation target in step S310, it may be changed to a size or shape which is associated in advance with a moving amount. For example, as the moving amount is larger, the size of the fixation target is changed to be larger to stabilize the vision fixation of the object. Also, as the moving amount is larger, the blinking cycle of the fixation target is changed to be shorter to draw the attention of the object. When the moving amount changes from a large value to a small one, the size of the fixation target becomes small, and the object can easily fix his vision at one point.

The pattern display screen 1401 on the measurement screen 1000 shown in FIG. 2 displays the display shape and size of the internal fixation target 191 and a currently selected one of the internal fixation target and external fixation target. This display is changed in accordance with switching between the internal fixation target and the external fixation target. In step S310, the shape of the fixation target pattern may be changed, as represented by the pattern 403, or the shape and size of the fixation target pattern may be changed, as represented by the pattern 404. Further, the external fixation target 324 may be turned on or blinked to switch the fixation target pattern without changing the display form of the internal fixation target 191. Alternatively, the external fixation target 324 may be turned on or blinked to switch the fixation target pattern without displaying the internal fixation target 191.

In step S310, the internal fixation target 191 may be blinked without changing the display form, or the internal fixation target 191 may be blinked together with change of the display form. Although not shown, the brightness or color of the fixation target may be changed. That is, a fixation target pattern corresponding to a moving amount is displayed by changing at least one of the shape, size, color, and brightness of the fixation target pattern into a shape, size, color, or brightness which is set in advance in accordance with the moving amount. Lighting may be switched in accordance with blinking of the fixation target or the moving amount. After that, the respective processes of the flowchart in FIG. 3 end.

In the embodiment, whether the vision fixation state of an eye to be examined is good or bad is determined based on the moving amount of the feature point of the eye to be examined, and the display form of the fixation target is changed in accordance with the vision fixation state. Thus, a fixation target suited to the object can be used to stabilize the vision fixation state of the eye to be examined. Since the vision fixation state of the eye to be examined stabilizes, degradation of the quality of an obtained OCT image and fundus image is reduced, and a stable measurement result can be obtained. The measurement time to select a fixation target suited to an object is shortened, and the burden on a patient can be reduced. Since the fixation target is automatically changed at a timing the object does not intend, the fixation target draws his attention and his vision fixation state can be improved.

In the embodiment, information (display content of the indicator) representing whether the vision fixation state of an eye to be examined is good or bad is changed in accordance with the moving amount of the feature point of the eye to be examined. While observing the display content of the indicator, the examiner can use a fixation target which is suited to the object and improves his vision fixation state, and can stabilize the vision fixation state of the eye to be examined. Accordingly, the vision fixation of the eye to be examined can be stabilized to shorten the measurement time, reducing the burden on the object.

(Second Embodiment)

In the first embodiment, the difference between the coordinates of a feature point on the first fundus image and those of the feature point on the second fundus image is used as the moving amount, and whether the vision fixation state of an eye to be examined is good or bad is determined based on the moving amount obtained by one calculation. The second embodiment will explain an arrangement in which the moving amount is calculated a plurality of times, the average value of them is used as the moving amount, and whether the vision fixation state of an eye to be examined is good or bad is determined.

Figure 7:
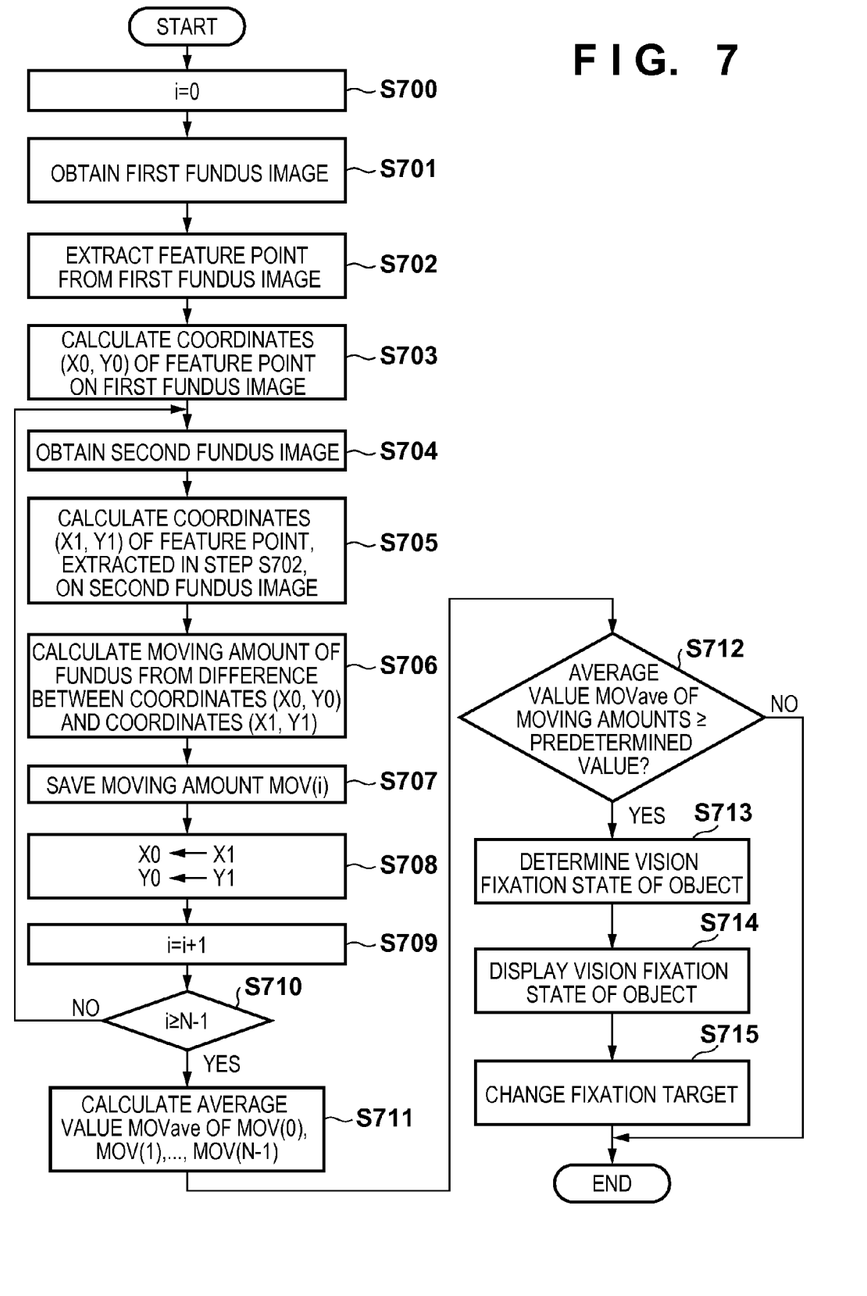
FIG. 7 is a flowchart exemplifying processing procedures by an ophthalmic apparatus according to the second embodiment.

Processing procedures by a control unit 925 of an ophthalmic apparatus 200 according to the second embodiment will be explained with reference to the flowchart of FIG. 7.

In step S700, the control unit 925 substitutes an initial value of 0 into a variable i. Processes in steps S701 to S706 are the same as those in steps S301 to S306.

In step S707, the control unit 925 functioning as an information obtaining unit saves the ith moving amount as MOV (i). In step S708, the control unit 925 substitutes X1 and Y1 into X0 and Y0, respectively, and sets the coordinates of a feature point on the second fundus image as reference coordinates for calculating a moving amount. In step S709, the control unit 925 determines that the loop has been processed once, and increments i by one.

In step S710, the control unit 925 determines whether the loop has been processed N times. If the control unit 925 determines that the loop has been processed N times (YES in step S710), the process advances to step S711. If the control unit 925 determines that the loop has not been processed N times (NO in step S710), the process returns to step S704. In step S711, the control unit 925 functioning as the information obtaining unit calculates the average value MOVave of moving amounts MOV(0), MOV(1), . . . , MOV(N−1) in respective loop operations.

In step S712, the control unit 925 determines whether the average value MOVave of the moving amounts is equal to or larger than a predetermined value. If the control unit 925 determines that MOVave is equal to or larger than the predetermined value (YES in step S712), the process advances to step S713. If the control unit 925 determines that MOVave is smaller than the predetermined value (NO in step S712), it determines that the vision fixation state of the object is good, and the process ends. Processes in steps S713 to S715 are the same as those in steps S308 to S310. After that, the respective processes of the flowchart in FIG. 7 end.

In the second embodiment, the moving amount is calculated a plurality of times, and the average value of them is set as the moving amount. Whether the vision fixation state of an eye to be examined is good or bad is determined based on this moving amount, and the display form of the fixation target is changed in accordance with the vision fixation state. Hence, a fixation target suited to an object at higher precision than that when a moving amount obtained by one calculation is used can be adopted, further stabilizing the vision fixation state of the eye to be examined.

(Third Embodiment)

Instead of calculating the moving amount of the fundus of an eye to be examined and determining whether the vision fixation of the eye to be examined is good or bad, as in the first and second embodiments, the database of normal eyes may be mounted to detect the lesion site of an eye to be examined and change the display of an internal fixation target 191 in accordance with the state of the lesion site. For example, when a lesion (disease) is detected in the macular region, the object cannot see well at the center. In this case, the fixation target pattern may be changed to one having a shape and size as represented by a pattern 404. More specifically, a control unit 925 functioning as an information obtaining unit may obtain the disease state of an eye to be examined as information about the eye to be examined from a fundus image. The control unit 925 also functioning as a change unit may change a fixation target pattern displayed by a fixation target display unit into a pattern appropriate for the object in accordance with the disease state.

The present invention is not limited to the above-described embodiments, and can be variously changed and modified without departing from the scope of the invention. For example, when it is determined in step S307 that the moving amount of the fundus is equal to or larger than a predetermined value, the control unit 925 may control the display unit 928 to display a display form for prompting the examiner to change the fixation target, instead of automatically changing the fixation target. The display form for prompting change of the fixation target is, for example, "the vision fixation state is bad, so change the size or shape of the fixation target." The display form for prompting change of the fixation target is arbitrary as long as the examiner can recognize that either the size or shape of the fixation target needs to be changed.

Also, the moving amount of the fundus may be associated in advance with the shape, size, color, brightness, and the like of a fixation target pattern. In this case, in accordance with the moving amount, the control unit 925 presents a concrete shape of the fixation target pattern such as "the vision fixation state is bad, so change the shape of the fixation target into a circle".

In this manner, the examiner is prompted to change the fixation target pattern in accordance with the vision fixation state. Even for a manual fixation target pattern, the examiner can quickly change the fixation target pattern. The vision fixation can be stabilized to shorten the measurement time, reducing the burden on the object and operator.

Although the fixation target pattern is changed based on the motion of the fundus of an eye to be examined or the like in the embodiments, the present invention is not limited to this. For example, the fixation target pattern may be changed based on the motion or disease of the anterior ocular segment of an eye to be examined.

In the above-described embodiments, the indicator 1204 functions when the moving amount of an eye to be examined is equal to or larger than a predetermined value, but the present invention is not limited to this. For example, even when the moving amount of an eye to be examined is smaller than the predetermined value, the indicator 1204 may function.

As described above, the fundus image of an eye to be examined is obtained, and information (for example, the moving amount between two fundus images or the position of a disease in the fundus image) about the eye to be examined is obtained from the obtained fundus image. In accordance with this information, the fixation target pattern is changed, or information (indicator) representing how much the vision fixation state is good or bad is changed. The examiner observes the indicator and can change the fixation target pattern to one suited to an object in accordance with whether the vision fixation state is good or bad. As a result, the vision fixation of the eye to be examined can be stabilized to shorten the measurement time, reducing the burden on the object.

According to the present invention, in ophthalmic imaging, the vision fixation of an eye to be examined can be stabilized to shorten the measurement time, reducing the burden on the object. The examiner refers to a display form representing the vision fixation state, and can appropriately switch the fixation target. Hence, the vision fixation of the eye to be examined can be stabilized to shorten the measurement time, reducing the burden on the object.

(Other Embodiments)

Aspects of the present invention can also be realized by a computer of a system or apparatus (or devices such as a CPU or MPU) that reads out and executes a program recorded on a memory device to perform the functions of the above-described embodiment(s), and by a method, the steps of which are performed by a computer of a system or apparatus by, for example, reading out and executing a program recorded on a memory device to perform the functions of the above-described embodiment(s). For this purpose, the program is provided to the computer for example via a network or from a recording medium of various types serving as the memory device (for example, computer-readable storage medium).

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2012-014581 filed on Jan. 26, 2012, which is hereby incorporated by reference herein in its entirety.

What is claimed is:

1. An ophthalmic apparatus comprising:
an image obtaining unit configured to obtain a first image and a second image of an eye to be examined;
an information obtaining unit configured to obtain, from the first image and the second image, a moving amount of the eye to be examined;
a fixation target display unit configured to display a fixation target pattern;
a comparison unit configured to compare the moving amount with a predetermined threshold; and
a change unit configured to change the fixation target pattern displayed by the fixation target display unit in a case where the comparison unit determines that the moving amount is larger than the predetermined threshold.

2. The apparatus according to claim 1, wherein the first image and the second image are fundus images of the eye to be examined, and
wherein the information obtaining unit obtains, as the moving amount, a distance value between a feature point of a fundus on the first image and a feature point of the fundus on the second image.

3. The apparatus according to claim 1, wherein the change unit changes at least one of a shape, size, color, and brightness of the fixation target pattern into a corresponding one of a predetermined shape, size, color, and brightness in accordance with the moving amount.

4. The apparatus according to claim 1, wherein the change unit switches the fixation target pattern between blinking and lighting in accordance with the moving amount.

5. The apparatus according to claim 1, further comprising a display control unit configured to display, on a display unit, a display form representing a vision fixation state of the eye to be examined,
wherein the change unit changes, in accordance with the moving amount, the display form representing the vision fixation state of the eye to be examined.

6. The apparatus according to claim 1, wherein the information obtaining unit obtains an average value of moving amounts of a fundus from a plurality of first fundus images and a plurality of second fundus images, and
wherein the change unit changes, in accordance with the average value of the moving amounts, the fixation target pattern displayed by the fixation target display unit.

7. An ophthalmic apparatus control method comprising:
obtaining a first image and a second image of an eye to be examined;
obtaining, from the first image and the second image, a moving amount of the eye to be examined;
comparing the moving amount with a predetermined threshold; and
changing a fixation target pattern displayed by a fixation target display unit in a case where it is determined that the moving amount is larger than the predetermined threshold.

8. A non-transitory computer-readable storage medium storing a computer program for causing a computer to execute each step of an ophthalmic apparatus control method defined in claim 7.

9. An ophthalmic apparatus comprising:
an image obtaining unit configured to obtain a first image and second image of an eye to be examined;
an information obtaining unit configured to obtain a moving amount of the eye to be examined from the first image and the second image;
a fixation target display unit configured to display a fixation target pattern;
a comparison unit configured to compare the moving amount with a predetermined threshold; and
a display control unit configured to display, on a display unit, information prompting a change of the fixation target pattern to be displayed by the fixation target display unit in a case where the comparison unit determines that the moving amount is larger than the predetermined threshold.

10. The apparatus according to claim 9, wherein the information prompting a change of the fixation target pattern is a message.

11. The apparatus according to claim 1, wherein the change unit changes at least one of a shape, size, color, and brightness of the fixation target pattern.

12. The apparatus according to claim 1, wherein the change unit changes a lighting state of the fixation target pattern.

* * * * *